United States Patent
Centola et al.

(10) Patent No.: US 10,028,821 B2
(45) Date of Patent: Jul. 24, 2018

(54) DEVICE FOR IMPLANTATION IN THE HEART OF A MAMMAL

(71) Applicant: NVT AG, Muri (CH)

(72) Inventors: Marcos Centola, Hechingen (DE); Emilia Kawa, Hechingen (DE); Thomas Bogenschuetz, Hechingen (DE)

(73) Assignee: NVT AG, Muri (CH)

( * ) Notice: Subject to any disclaimer, the term of this patent is extended or adjusted under 35 U.S.C. 154(b) by 0 days.

(21) Appl. No.: 14/678,376

(22) Filed: Apr. 3, 2015

(65) Prior Publication Data
US 2015/0282958 A1  Oct. 8, 2015

(30) Foreign Application Priority Data

Apr. 7, 2014 (EP) .................................... 14163731

(51) Int. Cl.
*A61F 2/07* (2013.01)
*A61F 2/24* (2006.01)
*A61B 90/00* (2016.01)

(52) U.S. Cl.
CPC ............... *A61F 2/07* (2013.01); *A61B 90/39* (2016.02); *A61F 2/2412* (2013.01); *A61F 2/2418* (2013.01); *A61B 2090/3966* (2016.02); *A61F 2/2475* (2013.01); *A61F 2220/0025* (2013.01); *A61F 2230/0069* (2013.01); *A61F 2250/0039* (2013.01)

(58) Field of Classification Search
CPC .......... A61F 2/07; A61F 2/2412; A61F 2/852; A61F 2/247; A61F 2/2418; A61F 2220/0025; A61F 2002/072; A61F 2002/0615; A61F 2/2475
See application file for complete search history.

(56) References Cited

U.S. PATENT DOCUMENTS

| | | | | |
|---|---|---|---|---|
| 5,725,572 A | * | 3/1998 | Lam | A61F 2/91 600/3 |
| 6,131,266 A | * | 10/2000 | Saunders | A61F 2/91 219/121.71 |
| 7,244,444 B2 | * | 7/2007 | Bates | A61F 2/06 424/400 |
| 2002/0198585 A1 | * | 12/2002 | Wisselink | A61F 2/07 623/1.11 |
| 2005/0251251 A1 | * | 11/2005 | Cribier | A61F 2/2412 623/2.11 |

(Continued)

FOREIGN PATENT DOCUMENTS

| | | |
|---|---|---|
| EP | 2522306 A1 | 11/2012 |
| WO | 2007121028 A2 | 10/2007 |
| WO | 2012018599 A1 | 2/2012 |

OTHER PUBLICATIONS

EP Search Report for EP Patent Application No. 14163731.4, dated Sep. 26, 2014, 4 pages.

*Primary Examiner* — Dinah Baria
(74) *Attorney, Agent, or Firm* — Reising Ethington, P.C.

(57) ABSTRACT

A device for implantation into the heart of a mammal and a method for treating tricuspid regurgitation using the device. The device includes two tubular stent members separated by a stent graft member which has a functional stented valve member attached thereto allowing unidirectional blood flow from the vena cava into the right atrium.

18 Claims, 4 Drawing Sheets

(56) References Cited

U.S. PATENT DOCUMENTS

2007/0233228 A1* 10/2007 Eberhardt ............. A61F 2/2415
                                                    623/1.13
2007/0244494 A1  10/2007 Downing
2012/0290069 A1* 11/2012 Ivancev .................. A61F 2/07
                                                    623/1.13

* cited by examiner

DEVICE FOR IMPLANTATION IN THE HEART OF A MAMMAL

This application claims priority from European patent application EP 14 163 731.4, filed on Apr. 7, 2014, the entire contents of which are incorporated herein by reference.

BACKGROUND

The present invention relates to a device for implantation in the heart of a mammal, with a generally tubular shape, and having a longitudinal axis, a first end and a second end, and a lumen permitting blood flow there through.

The present invention also relates to the use of such a device for treating tricuspid regurgitation in a mammal.

The human heart is subdivided by septa into right and left halves, and a constriction subdivides each half of the organ into two cavities, the upper cavity being called the atrium, the lower the ventricle, respectively. Thus, the heart consists of four chambers, i.e., right and left atria, and right and left ventricles. Via the four valves of the human heart, i.e. the aortic, mitral, tricuspid and pulmonary valves, a one-way blood flow through the (healthy) heart is maintained. Thus, the four heart valves make sure that blood always flows freely in a forward direction and that there is no backward leakage.

In the heart, blood flows from the right and left atria into the ventricles through the open tricuspid and mitral valves. When the ventricles are full, the tricuspid and mitral valves shut. This action, i.e. the closing of the tricuspid and the mitral valve, prevents blood from flowing backward into the atria while the ventricles contract. As the ventricles begin to contract, the pulmonic and aortic valves are forced open, thus pumping blood out of the ventricles: Blood present in the right ventricle passes through the open pulmonic valve into the pulmonary artery, and blood present in the left ventricle passes through the open aortic valve into the aorta where it is delivered to the rest of the body. When the ventricles finish contracting and begin to relax, the aortic and pulmonic valves shut. These valves prevent blood from flowing back into the ventricles.

With each heartbeat, this pattern is repeated, causing blood to flow continuously to the heart, lungs, and body. Due to their vital function, diseased or malfunctioning heart valves are a major threat for a person's life.

Several different kinds of valve disorders are known, such as stenosis, which occurs when a heart valve doesn't fully open due to stiff or fused leaflets preventing them from opening properly, or prolapse, where the valve flaps do not close smoothly or evenly but collapse backwards into the heart chamber they are supposed to be sealing off.

Valve regurgitation (backward flow) is also common problem, and occurs when a heart valve doesn't close tightly, as a consequence of which the valve does not seal and blood leaks backwards across the valve. This condition—also called valvular insufficiency—reduces the heart's pumping efficiency. When the heart contracts, blood is pumped forward in the proper direction but is also forced backwards through the damaged valve. As the leak worsens, the heart has to work harder to make up for the leaky valve and less blood may flow to the rest of the body. Depending on which valve is affected, the condition is called tricuspid regurgitation, pulmonary regurgitation, mitral regurgitation, or aortic regurgitation.

While mitral insufficiency has—likely due to its higher occurrence—been subject matter of many treatment approaches in recent years, tricuspid insufficiency, or rather its treatment has gained only little attention over the past years. Tricuspid insufficiency may be asymptomatic, however, common symptoms are, e.g. hepatomegaly, edema and jugular distenosis. As a result of the failure of the tricuspid valve to close properly, with each heart beat some blood passes from the right ventricle to the right atrium, the opposite of the normal direction. Although congenital causes of tricuspid insufficiency exist, most cases are due to annulus dilation and dilation of the right ventricle, and this dilation leads to a derangement of the normal anatomy and mechanics of the tricuspid valve and the muscles governing its proper function. The result is incompetence of the tricuspid valve.

However, isolated surgical tricuspid valve repair is seldom performed, and remains rather undertreated. Actually, most repairs are performed in the context with other planned cardiac surgeries.

The main therapy of tricuspid insufficiency is treatment of underlying cause, which is why in most cases surgery is not indicated since the root problem lies with a dilated or damaged right ventricle. Medical therapy with diuretics is the mainstay of treatment. Unfortunately, this can lead to volume depletion and decreased cardiac output. Indeed, one must often accept a certain degree of symptomatic tricuspid insufficiency in order to prevent a decrease in cardiac output. Treatment with medicines to reduce cardiac afterload may also be of benefit but a similar risk of depressed cardiac output applies.

Human heart valves may be replaced with mechanical valves, or with specially prepared heart valves from human or animal donors (known as bioprosthetic or tissue valves).

Bioprosthetic valves are sometimes called tissue valves and made from specially treated natural ("biological") valves. These valves come from two sources: human donors and animals. Valves from animal sources (usually cows or pigs) are very similar to those found in the human heart.

Surgical repair or replacement of the tricuspid valve carries a high operative mortality. When applying surgical means, tricuspid regurgitation is rectified either by replacement of the total valve with a replacement valve or by constriction of the valve ring with an annular remodeling ring, which involves rigid or flexible annular bands, which are intended to reduce annular size.

Due to the high risk of surgical operations and due to the fact that in many cases a surgery is even impossible to perform, e.g. if the patient is inoperable or operable only at a too high surgical risk, transcatheter techniques and devices for tricuspid regurgitation treatment have recently been developed; however, only limited experimental transcatheter data is available.

E.g., WO 2012/018599 A1 discloses a two valve caval stent for functional replacement of an incompetent tricuspid valve, which may be delivered by transcatheter placement. It comprises two stents connected by a bridge spanning the right atrium, and two valves anchored by the stents in the superior and inferior vena cavas.

Further, WO 2004/093638 discloses a device and methods for treatment of tricuspid regurgitation, where a first and a second stented valve are implanted at the superior and inferior vena cava. The device is intended to permit blood flow towards the right atrium of a patient and prevent blood flow in the opposite direction.

Nevertheless, the currently available devices and their handling imply complicated deployment methods, making a smooth and fast valve replacement difficult to achieve.

SUMMARY

Thus, it is an object of the present invention to provide for a device that facilitates the treatment of tricuspid regurgitation and overcomes the drawbacks of the prior art devices and treatment methods.

According to an aspect of the invention, this and other objects are solved by a device for implantation in the heart of a mammal, with a generally tubular shape, and having a longitudinal axis, a first end and a second end, and a lumen permitting blood flow there through, wherein the device comprises: (i) a first tubular stent member, sized and configured for implantation within the superior vena cava, and having a length, a diameter, a first and a second end, (ii) a second tubular stent member, sized and configured for implantation within the inferior vena cava, and having a length, a diameter, a first and a second end, wherein the second tubular stent member does not comprise a covering, (iii) a tubular stent graft member, having a length, a diameter, a first and a second stent graft member end, and comprising a covering being attached to a stent element, wherein the tubular stent graft member is fixedly assembled between the first and the second tubular stent members, such, that the second stent graft member end is attached to the first stent member's first end, and the first stent graft member end is attached to the second stent member's second end, wherein the stent graft member is sized and configured for implantation within the right atrium of the mammal's heart; and (iv) a stented valve member comprising a stent element and a valve, the valve being mounted on the stent element, wherein the stented valve member is fixedly mounted on the stent graft member, wherein the valve member is unidirectional, allowing blood to flow from the vena cava into the right atrium while blocking the blood flow in the opposite direction.

With the present device and its use in the treatment of tricuspid insufficiency, it is possible to securely and conveniently replace the tricuspid valve's function and effectively support the heart's function. The device spans a path through the heart from the vena cava superior to the vena cava inferior while simultaneously guaranteeing, by means of the fully functioning stented valve member, that the one-way blood flow from the right atrium to the right ventricle is maintained, and a backflow of the blood from the right ventricle into the right atrium can be prevented, thus effectively treating the tricuspid insufficiency.

The present device is easy to handle and deploy since only once device needs to be deployed—contrary to the devices currently available which either necessitate the deployment of two separate valves in the vena cava superior and vena cava inferior, or which apply a replacement annular ring of the natural valve.

Thus, with the present device, the overall deployment and valve replacement procedure, and, thus, the overall surgical operation, can be fast and easily accomplished.

Presently, and as generally understood, a "stent" is to be understood and referred to as a cylindrical or tubular, radially-expandable metal frame or body and means any device or structure that adds rigidity, expansion force, or support to a prosthesis, while "stent graft" refers to a prosthesis comprising a stent and a graft material associated therewith that forms a fluid-tight or substantially fluid-tight lumen through at least a portion of its length. The cylindrical/tubular body of stents/stent grafts is inserted into the vessel/organ to be treated and is expanded or self-expandable and fixed or fixes itself at the appropriate site in order to keep open the lumen of the vessel/organ.

The metal frame of the stent members and elements of the present device may be laser cut or woven or braided or knitted or comprise an otherwise interconnected metal mesh.

Accordingly, a "graft" material is a cylindrical liner that may be disposed on the stent's interior, exterior or both. A wide variety of attachment mechanisms are available to join the stent and graft together, including but not limited to, sutures, adhesive bonding, heat welding, and ultrasonic welding. Presently, a "covering" also may designate or is designating a graft material attached to a stent member, which is why a "stent graft" is presently, and throughout the relevant field, also designated as "covered stent" or "covered stent graft."

Stent grafts generally comprise, for example, a series of stent elements or, respectively, a wire framework made of a self-expanding material. In this context, stents are understood to be individual self-expanding elements. The self-expanding elements or, respectively, the wire framework are connected to each other by a textile or PTFE tube, called a graft sleeve, to form a functional unit and in this way, analogous to the stents described above, they form a tubular body that supports the vessel walls The stent elements of the stent graft may represent single metal rings forming a metal mesh, the rings meandering circumferentially and being disposed successively in the graft member's longitudinal axis/direction, wherein the metal rings have a Z-shaped profile with pointed arches pointing alternately toward the proximal end and distal end of the device.

According to one aspect of the invention, the tubular stent graft member located between the two, i.e. the first and second tubular stent members, forms a fluid-tight or substantially fluid-tight sealing, only permitting unidirectional blood flow towards the right ventricle via the stented valve member mounted thereupon.

Also, and according to another aspect of the invention, the second stent member does not comprise a covering or graft material, thus providing an anchor for the device in the vena cava inferior, whilst guaranteeing that blood flow into vessels which branch off the vena cava inferior are not blocked. The first stent member, on the other hand may be covered or not, and is, according to a preferred embodiment, not covered by a graft material/covering. Accordingly, the first stent member provides for anchoring means of the device within the vena cava superior.

The present stent/stent member can be made of or comprise any suitable material, including but not limited to biocompatible metals, implantable quality stainless steel wires, nickel and titanium alloys, in particular nitinol, and biocompatible plastics attached to a graft.

Any suitable fluid tight or substantially fluid-tight graft material can be used. In a preferred embodiment, the graft material is a biocompatible fabric, including but not limited to woven, knitted or otherwise fabricated material, such as polyester, such as polyethylene terephthalate, fluorinated polymers, such as polytetrafluoroethylene (PTFE), expanded PTFE (ePTFE), polyvinylidene fluoride, polysiloxane, including polydimethyl siloxane, polyurethanes, including polyetherurethanes, polylactide, polyglycolide and copolymers thereof.

Also, materials that are not inherently biocompatible may be used when previously subjected to surface modifications in order to render the materials biocompatible.

Further, biomaterial as mammal (i.e. bovine, porcine) derived pericardium or submucosa of small intestine (SIS) or any other cross linked bio-material tissue suitable to be used as a graft material may be employed.

According to one aspect of the invention, the (covered) stent graft member can be made of any suitable material, including but not limited to polytetrafluoroethylene (ePTFE) lined nickel-titanium alloy (nitinol) stent.

The components of the device, i.e. the first and second stent members and the stent graft member comprising the stented valve member can be variously sized (i.e. length, diameter, etc.) as suitable for an intended use and as depending on the respective condition of the patient's heart, and are preferably larger in diameter than the inner vessel diameter the members of the device are to be placed in.

It is to be understood that the covering and/or the stent element of the stent graft member at the site where the stented valve member is attached to the stent graft member allow for a fluid path into and out of the valve in the direction towards the atrium. This can be accomplished by means of an opening in the covering, sized and fitted for the stented valve member attached thereto, and/or meshes of the stent graft's stent element.

According to another aspect of the device of the invention, the device further comprises visualization elements, in particular radio-opaque markers, wherein the visualization elements are attached to the device at one or more of the following elements of the device: at the site where the stent graft member's first end is attached to the second stent member's second end, at the site where the stent graft member's second end is attached to the first stent member's first end, and/or at the fixation site of the stented valve member to the stent graft member.

Presently, "visualization elements" shall mean any suitable aid attached or otherwise provided on the device facilitating the accurate placement of the device. According to one aspect of the invention, those visualization elements are radiopaque markers comprising or consisting of any suitable material, such as, e.g., gold, tantalum, platinum.

The visualization elements may, e.g., take the form of gold bands or singular elements at the respective preferred locations of the device, or represent directional elements or markers, e.g. in the shape of a letter, such as "E" or "S" or "J" or "L" or any other suitable letter or form for indicating direction and orientation of the device.

The visualization elements are, in one embodiment, arranged over the circumference at the site where the stent graft element and the tubular stent elements are attached to one another, and/or at the site where the stented valve member is attached to the stent graft element.

According to another aspect of the invention, at least one of the following, the first stent member, the second stent member, the stent element of the stent graft member, and/or the stent element of the stented valve member is/are self-expanding, wherein the device is configured, such, that it is convertible from a compressed state for introducing the device into a heart of a mammal to an expanded state within the heart.

Accordingly, the stent elements of the device are preferably self-expanding, although the device—or rather its stent/stent graft members/elements, may also be, e.g., balloon-expandable. The stent members allow for radial force fixation within the vena cava.

According to a preferred embodiment, the present device, along its longitudinal axis, varies in its diameter. With this embodiment, the different diameters and conditions of the vessels, in particular the vena cava can be respected.

Further, in a preferred embodiment, the first stent member's diameter is, in the expanded state of the device, smaller than the second stent member's diameter.

In this embodiment, i.e. where the first stent member has—in its expanded state—a smaller diameter than the second stent member, the diameters are reflecting the larger diameter of the vena cava inferior as compared to the diameter of the vena cava superior. Thus, a secure fixation of the device in the vena cava can be achieved.

In another embodiment of the device according to the invention, the diameter of each, the first stent member, the second stent member and/or the stent graft member, vary along the respective lengths for the members.

With this embodiment, an even finer adjustment of the device to the respective vessel conditions and forms can be guaranteed.

According to one aspect of the invention, in the present device, the valve is a biological valve comprising one, two or three leaflets, preferably three.

The healthy human tricuspid valve comprises three leaflets, or cusps, named after their positions: anterior, posterior and septal. Thus, according to one aspect, the valve of the stented valve mounted on the stent graft member also comprises three leaflets, and thus, represents a tricuspid valve, whilst also a valve having only two leaflets and, having, thus, a "bicuspid" architecture, or with even one leaflet, i.e. a monocuspid valve, can be used with the device according to the invention. Such valves can be created from human or animal donors. They can be created, e.g., from pericardium of human or any mammal, or from native leaflets from the heart or veins, or from any other biological material suitable for the intended purpose. Generally speaking, such valves are also called biological or tissue valves—as contrary to mechanical valves.

Accordingly, in a preferred embodiment, the biological valve comprises or consists of a material that is selected from animal pericardium, in particular porcine, bovine, equine pericardium, or from native leaflets from human heart or veins.

The invention also relates to the use of the present device for treating tricuspid regurgitation in a mammal, as well as to a method for treating tricuspid regurgitation in a mammal, comprising the step of delivering and/or implanting the present device to a position within the heart of a patient in need thereof in order to replace or support the native tricuspid valve of said patient.

The present device can be either surgically implanted or delivered by transcatheter methods. In the latter case, i.e. with a transcatheter method, the device is loaded onto a suitable deployment catheter, there being compressed by a retractable sheath or tube. The deployment catheter is inserted into the heart of a patient whose tricuspid valve needs replacement or support. The deployment catheter having the device loaded thereon in a compressed state, is advanced via the jugular vein into the vena cava superior into the right atrium and into the vena cava inferior, as far as the second tubular stent member is placed into the vena cava inferior, the stent graft member within the right atrium and the first tubular stent member into the vena cava superior. Alternatively, the deployment catheter having the device loaded thereon in a compressed state can be advanced via the femoral vein into the vena cava inferior into the right atrium and into the vena cava superior, as far as the first tubular stent member is placed into the vena cava superior, the stent graft member within the right atrium and the second tubular stent member into the vena cava inferior. Correct placement can be monitored via the visualization elements.

Upon correct placement, the sheath or the otherwise compressing means is retracted to stepwise release the present device, upon which action the stent members of the device can expand and fixate the device in the vena cava superior and inferior, respectively.

Since also the stent graft member is released, the stented valve element mounted thereon can operate as soon as the compressing means are retracted.

Further advantages and features are set forth in the following description and in the attached figures.

It will be understood that the aforementioned features and the features still to be explained below can be used not only in the respectively specified combination but also in other combinations or on their own, without departing from the scope of the present invention.

DRAWINGS

The aforementioned features of the invention and the features still to be explained below are shown in the figures, in which.

DESCRIPTION

Figure 1:
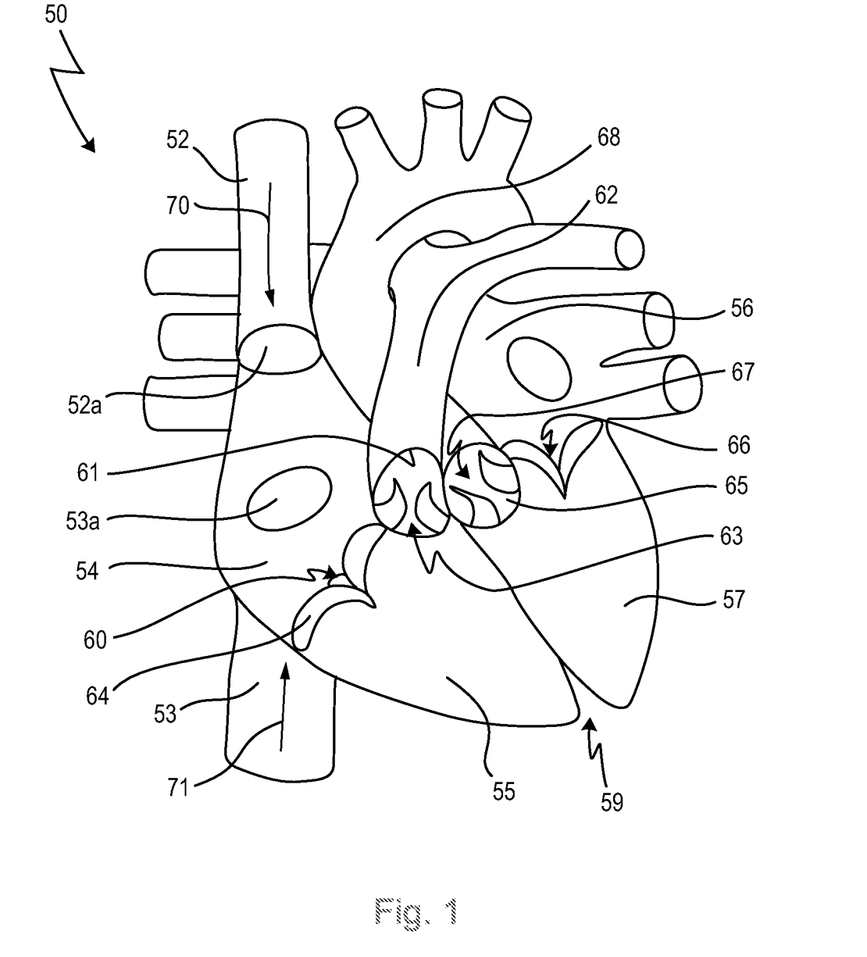
FIG. 1 shows a schematic drawing of a human heart.

In FIG. 1, a human heart 50 is depicted, having a right atrium 54, a right ventricle 55, a left atrium 56 and a left ventricle 57. Also depicted in FIG. 1 is a portion of the vena cava superior 52, entering the heart 50 via the right atrium 54, and a portion of the vena cava inferior 53.

In more detail, the superior vena cava 52 returns the blood from the upper half of the body, and opens into the upper and back part of the right atrium 54, the direction of its orifice 52a being downward and forward. Its orifice 52a has no valve.

The inferior vena cava 53, which has a larger diameter than the superior vena cava 52, returns the blood from the lower half of the body, and opens into the lowest part of the right atrium 54, its orifice 53a being directed upward and backward, and guarded by a rudimentary valve, the valve of the inferior vena cava (Eustachian valve, not shown).

The right ventricle 55 has a triangular form, and extends from the right atrium 54 to near the apex 59 of the heart 50.

The right atrioventricular orifice (not depicted in FIG. 1) is the large oval aperture of communication between the right atrium 54 and ventricle 55, and is guarded by the tricuspid valve 60.

The opening 61 of the pulmonary artery 62 is circular in form, and is placed above and to the left of the atrioventricular opening; it is guarded by the pulmonary valves 63.

The tricuspid valve 60 consists of three generally triangular cusps or segments or leaflets 64, the anterior, posterior and medial or septal cusp. Their bases are attached to a fibrous ring (not depicted in FIG. 1) surrounding the atrioventricular orifice and are also joined to each other so as to form a continuous annular membrane. Their atrial surfaces are directed toward the blood current from the atrium 54, while their ventricular surfaces are directed toward the wall of the ventricle 55; together with the apices and margins of the cusps, they give attachment for the chordae tendineae (not depicted in FIG. 1).

As discussed above, the function of the tricuspid valve is to prevent back flow of blood into the right atrium 54; arrows 70 and 71 indicate normal blood flow into the right atrium 54.

The left atrium 56 is smaller than the right atrium 54. The left ventricle 57 is longer and more conical in shape than the right ventricle 55. The left atrioventricular opening (mitral orifice, not depicted in FIG. 1) is placed to the left of the aortic orifice 65, and is guarded by the bicuspid or mitral valve 66.

The aortic opening 65 is a circular aperture, in front and to the right of the atrioventricular opening, and its orifice is guarded by the three aortic valves 67. Reference number 68 designates the aorta.

Tricuspid regurgitation is not uncommon in the tricuspid valve 60, and means that blood from the right ventricle 55 flows back into the right atrium 54 upon contraction of the right ventricle 55 due to the tricuspid valve 60 not properly closing.

Figure 2:
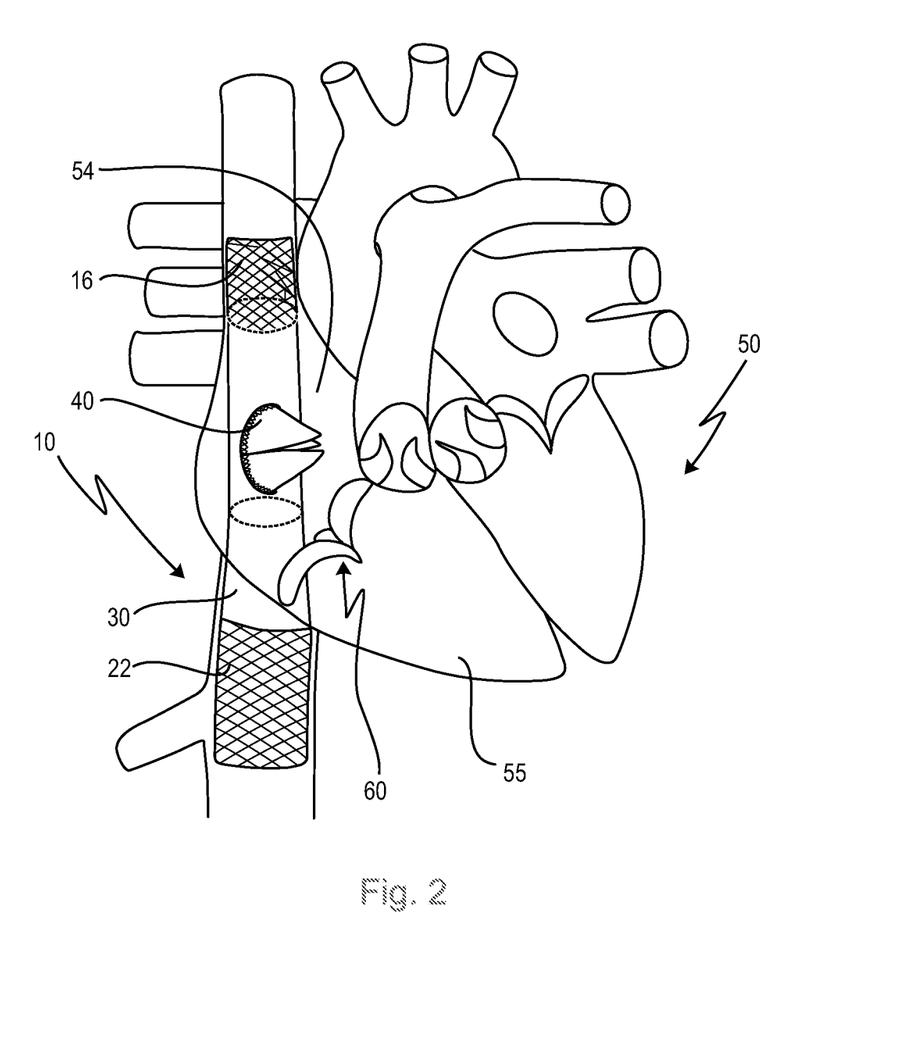
FIG. 2 shows a schematic drawing of an exemplary embodiment of the present device placed in the correct position in the heart of FIG. 1.

With the present device, tricuspid regurgitation is to be treated, and placement of an exemplary embodiment of the present device is depicted in the attached FIG. 2.

FIG. 2 shows the schematic drawing of the heart as already depicted in FIG. 1. For better understanding, FIG. 2 does not include all of the reference numbers as designated in FIG. 1, but is meant to show the same features of the human heart 50.

Figure 3:
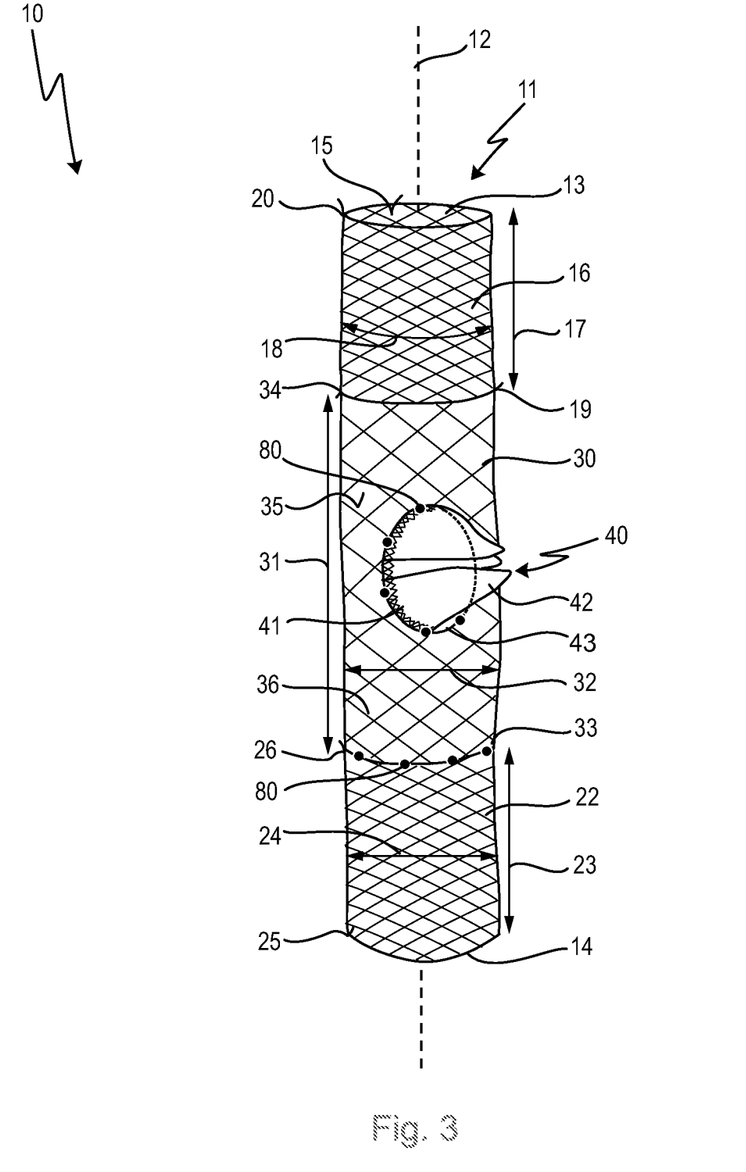
FIG. 3 shows a schematic drawing of the embodiment as shown in FIG. 2, outside the heart and in enlarged detail.

As can be seen in FIG. 2, an embodiment of the present device 10 is placed in the expanded state in the human heart 50. The device as such is shown in more detail in FIG. 3, and in the following reference will be made to both, FIGS. 2 and 3; for the sake of better understanding, not all of the features of the device designated in FIG. 3 are designated in FIG. 2, however, the features are nevertheless the same.

Device 10 comprises a general tubular shape 11, and has a longitudinal axis 12, a first end 13 and a second end 14, with a lumen 15 extending in between and permitting blood flow there through.

The device 10 comprises a first tubular stent member 16, a second stent member 22, and a stent graft member 30 placed in between the first and second tubular stent member. The first tubular stent member 16 has a length 17, a diameter 18, and a first and a second end 19, 20, respectively. Length 17 and diameter 18 of the first tubular stent member 16 are such that the stent member 16 can securely anchor the device's first end 13 within the vena cava superior 52.

Also, the second stent member 22 has a length 23, a diameter 24, a first and a second end 25, 26, respectively. Length 23 and diameter 24 of the second tubular stent member 22 are such that the stent member 22 securely anchors the device's second end 14 within the vena cava inferior 53.

The stent graft member 30 has a length 31, a diameter 32, a first and a second end 33, 34, respectively, and comprises a covering or graft 35 which is attached to or lines a stent element 36, which stent element 36 represents a tubular metal frame. The length of the stent graft member 30 is designed such that it lies within the right atrium 54 of the heart 50 of a patient who is to be treated. The covering or graft 35 is made of or comprises a biocompatible material and provides for a leak-tight or substantially leak-tight closure of the tubular device in the right atrium 54.

Stent graft member 30 further comprises a stented valve member 40, mounted or attached to stent graft member 30. Stented valve member 40 comprises a stent element 41 and a valve 42, the valve 42 being mounted on the stent element 41. Stented valve member 40 represents a unidirectional valve, allowing blood to flow from the vena cava 52/53 into the right atrium 54 while blocking the blood flow in the opposite direction, i.e. blocks flow from the right ventricle 55 into the atrium 54. The stented valve member 40 will be described in more detail with reference to FIG. 4 below.

The first and second stent members 16, 22 and the stent graft member 30 are fixedly connected with each other as follows and form, thus, a tubular one-piece device:

At its first end 19, the first stent element 16 is attached to the stent graft member's 30 second end 34. The stent graft member's 30 first end 33 is attached to the second end 26 of the second stent member 22.

Device 10 further comprises visualization elements 80, which, in the embodiment shown in FIGS. 2 and 3, are placed at the site where the stent graft member's first end 33 is attached to the second stent member's 22 second end 26, at the site where the stent graft member's second end 34 is attached to the first stent member's 16 first end 19, and/or at a fixation site 43 of the stented valve member 40 to the stent graft member 30. Preferably, and as shown in the figures, the visualization elements 80 are placed circumferentially around the tubular form 11 at the respective sites.

Figure 4:
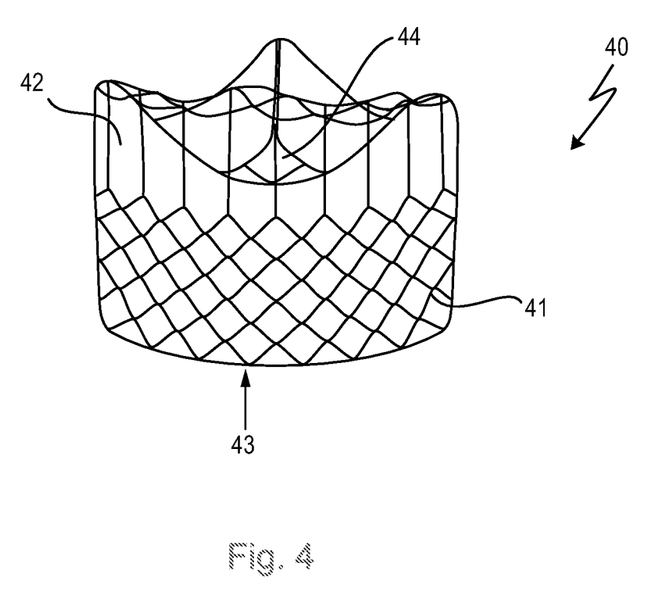
FIG. 4 shows an enlarged schematic drawing of an isolated exemplary stented valve member of the present device.

FIG. 4 is an enlarged schematic drawing of an isolated exemplary stented valve member 40 which according to the invention is mounted onto the stent graft member 30.

As can be seen in FIG. 4 in more detail, the stented valve member 40 comprises a stent element 41 and a valve 42, the valve 42 being mounted onto the stent element 41. The valve 42 comprises, in the exemplary embodiment shown in the figures, three leaflets or cusps 44.

As described in the general section, the valve can also be bi- or monocuspid, and may be created from human or animal pericardium or from native valves or veins or similar.

It is to be understood that the stent element 36 and the covering or graft 35 of the stent graft member 30 are designed, such, that upon attachment of the stented valve member 40 to the stent graft member 30, a blood flow via the attachment site is possible. This means that the graft material or covering 35 of the stent graft member 30 has an opening in its circumference sized and fitted for the circumference of the stented valve member 40. When using singular stent elements only connected to each other via the covering 35, the opening may be between two stent elements. Otherwise, e.g. when using a metal mesh as stent element for the stent graft element 30, the opening in the covering 35 may be formed in/by one or more meshes.

The invention claimed is:

1. Device for implantation in the heart of a mammal, with a generally tubular shape, and having a longitudinal axis, a first end and a second end, and a lumen permitting blood flow there through, wherein the device comprises
    a first tubular stent member, so dimensioned as to be implantable within the superior vena cava, and having a length, a diameter, a first end and a second end, wherein the first tubular stent member does not comprise a covering on an interior of the first tubular stent member or an exterior of the first tubular stent member,
    a second tubular stent member, so dimensioned as to be implantable within the inferior vena cava, and having a length, a diameter, a first end and a second end, wherein the said second tubular stent member does not comprise a covering on an interior of the second tubular stent member or an exterior of the second tubular stent member,
    a tubular stent graft member, having a length, a diameter, a first stent graft member end, a second stent graft member end, and an opening along the length, and comprising a covering being attached to a stent element, wherein the tubular stent graft member is fixedly assembled between the first tubular stent member and the second tubular stent member, such, that the second stent graft member end is attached to the first tubular stent member's first end, and the first stent graft member end is attached to the second tubular stent member's second end, wherein the tubular stent graft member is so dimensioned as to be implantable within the right atrium of the mammal's heart; and
    a stented valve member comprising a stent element and a valve, the valve being mounted on the stent element, wherein the stent element of the stented valve member is fixedly mounted on the stent element of the tubular stent graft member such that the stent element of the stented valve member is sized and fitted to align with the opening of the tubular stent graft member, wherein the stented valve member is unidirectional, allowing blood to flow from the vena cava into the right atrium in a direction generally perpendicular to the lumen while blocking the blood flow in an opposite direction, wherein the stented valve member comprises a material that is selected from animal pericardium or from native leaflets from a human heart or veins, and wherein the valve is configured to function as a tricuspid valve of a human heart, to prevent regurgitation of a natural tricuspid valve when implanted.

2. The device of claim 1, further comprising visualization elements, preferably radio-opaque markers, wherein the visualization elements are attached to the device at one or more of the following sites of the device: at the site where the first stent graft member end is attached to the second end of the second tubular stent member, at the site where the second stent graft member end is attached to the first end of the first tubular stent member, and/or at the fixation site of the stented valve member to the tubular stent graft member.

3. The device of claim 2, wherein the visualization elements are radio-opaque markers.

4. The device of claim 1, wherein at least one of the first tubular stent member, the second tubular stent member, the stent element of the tubular stent graft member, and/or the stent element of the stented valve member is/are self-expanding, and wherein the device is configured, such, that it is convertible from a compressed state for introducing the device into a heart of a mammal to an expanded state within the heart.

5. The device of claim 1, wherein the device, along said longitudinal axis, varies in its diameter.

6. The device of claim 1, wherein the diameter of the first tubular stent member is, in the expanded state of the device, smaller than the diameter of the second tubular stent member.

7. The device of claim 1, wherein the diameter of the first tubular stent member, the second tubular stent member or the tubular stent graft member, vary along the respective length of the first tubular stent member, the second tubular stent member, or the tubular stent graft member.

8. The device of claim 1, wherein the valve is biocompatible and comprises one, two or three leaflets.

9. The device of claim 1, wherein the valve comprises an animal pericardium material that is selected from porcine, bovine, or equine pericardium.

10. The device of claim 1, wherein the covering of the tubular stent graft member comprises a material selected from at least one of the following: polyester, polytetrafluoroethylene (PTFE), expanded PTFE (ePTFE), polyvinylidene fluoride, polysiloxane, polyurethane, polylactide, polyglycolide and copolymers thereof.

11. The device of claim 1, wherein at least one of the first tubular stent member, the second tubular stent member, the stent element of the tubular stent graft member, and/or the stent element of the stented valve member is/are woven, braided or laser-cut.

12. The device of claim 1, wherein the stent element of the tubular stent graft member is fixedly assembled between the first tubular stent member and the second tubular stent member.

13. Method for treating tricuspid regurgitation in a mammal, the method comprising the step of deploying, delivering or implanting the device of claim 1 in a position within the heart of a patient in need thereof in order to replace or support the native tricuspid valve of said patient.

14. The method of claim 11, wherein the device is surgically implanted.

15. The method of claim 14, wherein the method, comprises the following steps:
loading the device onto a deployment catheter, and, thereupon, holding the device in a compressed state by a retractable sheath;
advancing the deployment catheter having the device loaded thereon in a compressed state, via a jugular vein into a vena cava superior into the right atrium and into the vena cava inferior of the heart of the patient, in order to place the second tubular stent member into the vena cava inferior, the stent graft member within the right atrium and the first tubular stent member into the vena cava superior; and
deploying the device in the heart of the patient by retracting the sheath in order to replace or support the native tricuspid valve of said patient.

16. The method of claim 14, wherein the method, comprises the following steps:
loading the device onto a deployment catheter, and, thereupon, holding the device in a compressed state by a retractable sheath;
advancing the deployment catheter having the device loaded thereon in a compressed state via a femoral vein into a vena cava inferior into the right atrium and into the vena cava superior of the heart of the patient, in order to place the first tubular stent member into the vena cava superior, the stent graft member within the right atrium and the second tubular stent member into the vena cava inferior; and
deploying the device in the heart of the patient by retracting the sheath in order to replace or support the native tricuspid valve of said patient.

17. The method of claim 11, wherein the device is delivered by transcatheter methods.

18. Device for implantation in the heart of a mammal, with a generally tubular shape, and having a longitudinal axis, a first end and a second end, and a lumen permitting blood flow there through, wherein the device comprises
a first tubular stent member, so dimensioned as to be implantable within the superior vena cava, and having a length, a diameter, a first end and a second end, wherein the first tubular stent member does not comprise a covering on an interior of the first tubular stent member or an exterior of the first tubular stent member,
a second tubular stent member, so dimensioned as to be implantable within the inferior vena cava, and having a length, a diameter, a first end and a second end, wherein the said second tubular stent member does not comprise a covering on an interior of the second tubular stent member or an exterior of the second tubular stent member,
a tubular stent graft member, having a length, a diameter, a first stent graft member end and a second stent graft member end, and comprising a covering being attached to a stent element, wherein the tubular stent graft member is fixedly assembled between the first tubular stent member and the second tubular stent member, such, that the second stent graft member end is attached to the first tubular stent member's first end, and the first stent graft member end is attached to the second tubular stent member's second end, wherein the tubular stent graft member is so dimensioned as to be implantable within the right atrium of the mammal's heart; and
an annular stented valve member comprising a stent element and a valve, the valve being mounted on the stent element, wherein the annular stented valve member is fixedly mounted on the tubular stent graft member so as to project outwardly from and generally perpendicular to the lumen, wherein the annular stented valve member is unidirectional, allowing blood to flow from the vena cava into the right atrium while blocking the blood flow in an opposite direction, wherein the annular stented valve member comprises a material that is selected from animal pericardium or from native leaflets from a human heart or veins, and wherein the valve is configured to function as a tricuspid valve of a human heart, to prevent regurgitation of a natural tricuspid valve when implanted.

* * * * *